US008700334B2

United States Patent
Parida

(10) Patent No.: US 8,700,334 B2
(45) Date of Patent: Apr. 15, 2014

(54) METHODS AND SYSTEMS FOR RECONSTRUCTING GENOMIC COMMON ANCESTORS

(75) Inventor: Laxmi Priya Parida, Mohegan Lake, NY (US)

(73) Assignee: International Business Machines Corporation, Armonk, NY (US)

( * ) Notice: Subject to any disclaimer, the term of this patent is extended or adjusted under 35 U.S.C. 154(b) by 1690 days.

(21) Appl. No.: 11/495,535

(22) Filed: Jul. 31, 2006

(65) Prior Publication Data

US 2008/0027656 A1     Jan. 31, 2008

(51) Int. Cl.
*G06F 19/00* (2011.01)
*G06F 19/14* (2011.01)

(52) U.S. Cl.
USPC .............................................. 702/19; 702/20

(58) Field of Classification Search
None
See application file for complete search history.

(56) References Cited

U.S. PATENT DOCUMENTS

2007/0294038 A1* 12/2007 Landau et al. .................. 702/20

OTHER PUBLICATIONS

Landau et al., "Gene Proximity Analysis across Whole Genomes via PQ Trees", 2005, Journal of Computational Biology, vol. 12, No. 10, pp. 1289-1306.*
Bergeron et al., "Reconstructing Ancestral Gene Orders Using Conserved Intervals", 2004, Proceedings $4^{th}$ Workshop on Algorithms in Bioinformatics (WABI), pp. 14-25.*
Landau et al. (Using PQ Trees for Comparative Genomics in Lecture Notes in Computer Science vol. 3527, pp. 128-143; Springer Verlag date: Proceedings held Jun. 19-22, 2005).*
Xin He, et al. "Identifying Conserved Gene Clusters in the Presence of Orthologous Groups", RECOMB'04, Mar. 27-31, San Diego, CA, pp. 272-280, (2004).
Ann Bergeron, et al., "On the Similarity of Sets of Permutations and its Applications to Genome Comparison", COCOON 2003, LNCS 2697, pp. 68-79.
Ann Bergeron, et al., "The Algorithmic of Gene Teams", WABI 2002, LNCS 2452, pp. 464-476.

\* cited by examiner

*Primary Examiner* — Lori A Clow
(74) *Attorney, Agent, or Firm* — Vazken Alexanian; McGinn IP Law Group, PLLC

(57) ABSTRACT

Methods and systems for reconstructing common ancestors include determining a PQ tree structure based upon permutations between two genomes, and reconstructing an ancestor genome based upon the PQ tree structure. A PQ tree includes a first internal node (P node) that allows a permutation of the children thereof, and a second internal node (Q node) that maintains a unidirectional order of the children thereof.

14 Claims, 9 Drawing Sheets

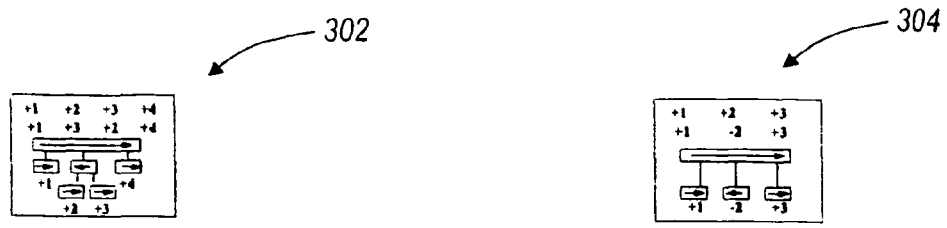
Fig. 3
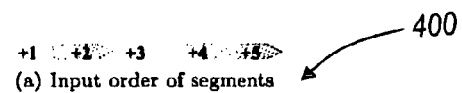
(a) Input order of segments
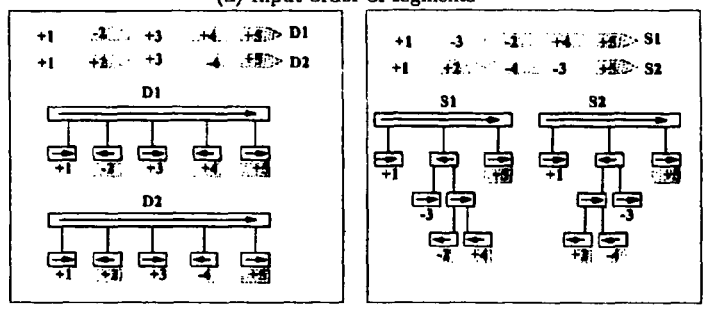
(b) The inversion segments are disjoint (c) The inversion segments straddle
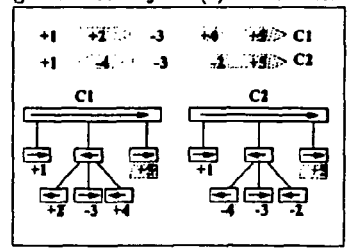
(d) One inversion segment is contained in the other
Fig. 4

(a) translocation & inversion
(b) translocation
(c) translocation & inversion
(d) translocation

```
Initialize Π_w ← Π
For each π ∈ Π Lpi(π) ← {π}, Chld(π) ← φ

While (Π_w ≠ φ) {
    Π_new ← φ
    For each π_1, π_2 ∈ Π_w
        If (Lpi(π_1) ∩ Lpi(π_2) = φ)           //prune acyclic structures
            S = P_c(π_1, π_2)                    //compute common parents
            For each π ∈ t
                If (π ∉ Π_new) Chld(π) ← φ
                If (π ≠ π_1) Chld(π) ← Chld(π) ∪ {π_1}
                If (π ≠ π_2) Chld(π) ← Chld(π) ∪ {π_2}
            Π_new ← Π_new ∪ S
    For each π ∈ Π_new
        A[π] ← s(+(Chld(π)))                    //update subtrees of new nodes
    If (Π_new = φ) Π_w ← φ                      //terminate if no new π's
    Else Π_w ← Π_w ∪ Π_new                      //add the new ones
}
```

Fig. 7

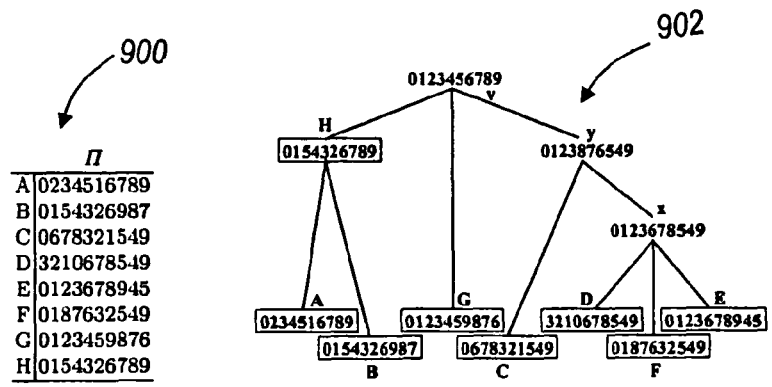

Fig. 9

| $\Pi$ | iteration 1 | iteration 2 | iteration 3 |
|---|---|---|---|
| $A$=0234516789 | $H \in P_1(A,B)$ | | |
| $B$=0154326987 | $(z \in P_1(A,B))$=0234516987 | | |
| $H$=0154326789 | | | $(v \in P_1(H,y,G))$ |
| $C$=0678321549 | | $(y \in P_1(C,x))$ | = 0123456789 |
| $D$=3210678549 | $(x \in P_1(D,E,F))$=0123678549 | = 0123876549 | |
| $E$=0123678945 | $(x_2 \in P_1(D,E))$=3210678945 | $(y_2 \in P_1(C,x))$ | $(u \in P_1(H,G))$ |
| $F$=0187632549 | $(x_3 \in P_1(E,F))$=0187632945 | = 0876321549 | = 0154329876 |
| $G$=0123459876 | | | |

(1)

| $\pi$ | $s(\pi)$ | $L_{pi}(s(\pi))$ |
|---|---|---|
| $x$ | $DEF3x$ | $D,E,F$ |
| $x_2$ | $DE2x_2$ | $D,E$ |
| $x_3$ | $EF2x_3$ | $E,F$ |
| $z$ | $AB2z$ | $A,B$ |
| $y$ | $CDEF3x2y$ | $C,D,E,F$ |
| $y_2$ | $CDEF3x2y_2$ | $C,D,E,F$ |
| $u$ | $AB2HG2u$ | $A,B,G,H$ |
| $v$ | $AB2HCDEF3x2yG2v$ | $A,B,C,D,E,F,G,H$ |

Fig. 12
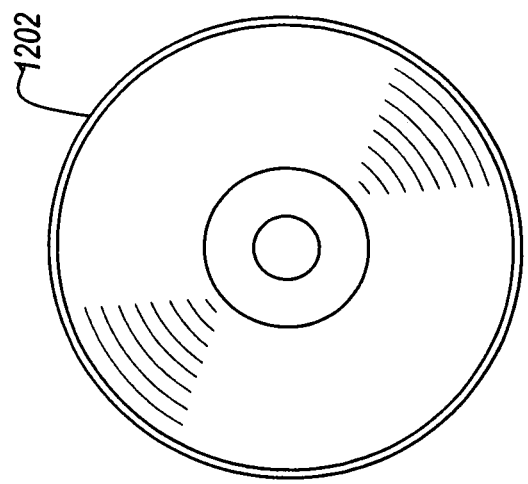
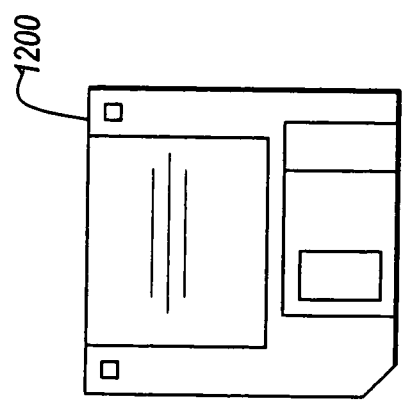

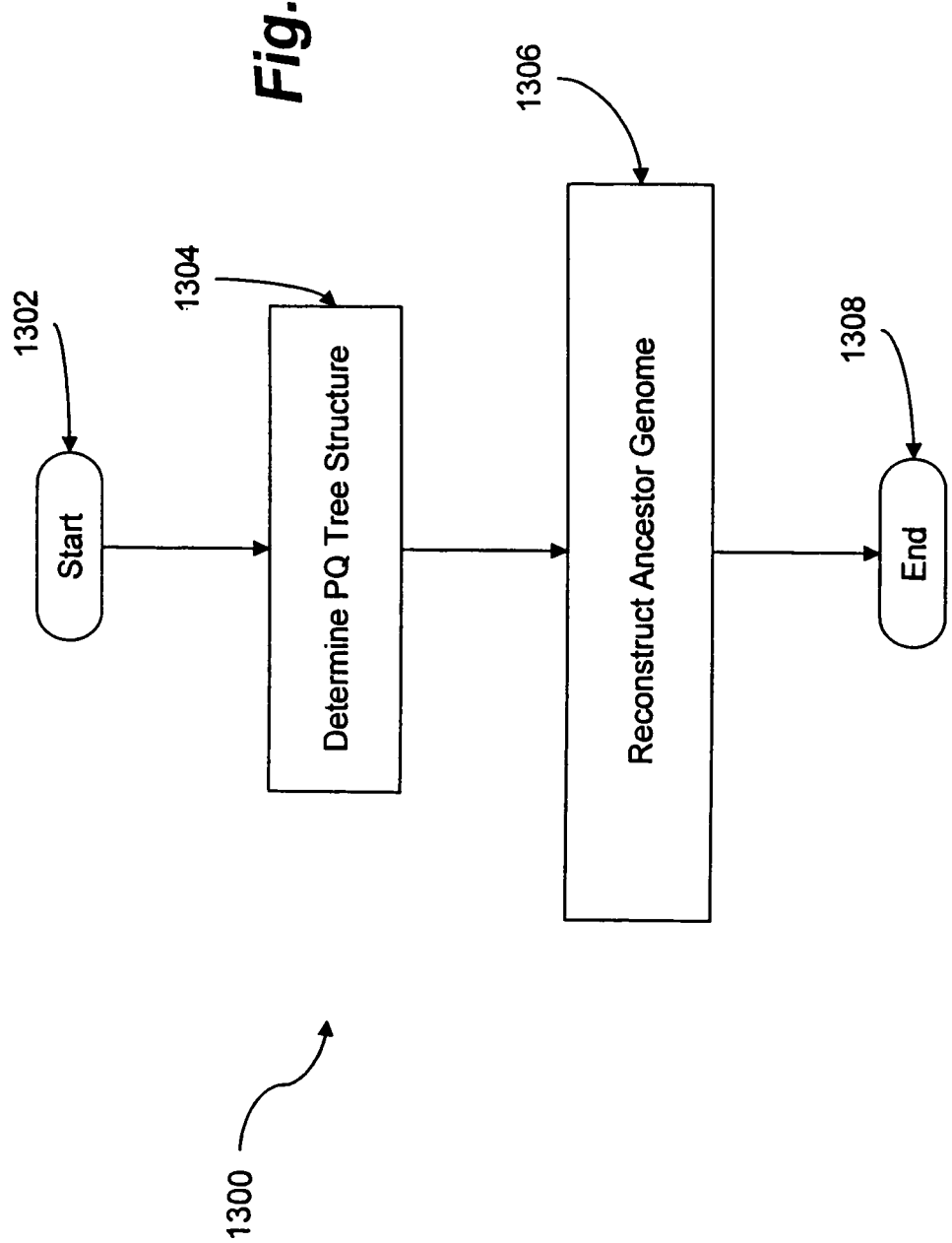

METHODS AND SYSTEMS FOR RECONSTRUCTING GENOMIC COMMON ANCESTORS

BACKGROUND OF THE INVENTION

1. Field of the Invention

The present invention generally relates to methods and systems for reconstructing genomic ancestors. In particular, the present invention relates to methods and systems that reconstruct genomic common ancestors using a PQ tree.

2. Description of the Related Art

Various international efforts are underway to catalog the genomic similarities and variations in the human population. As the study progresses, data in the form of genomic markers is becoming available, with due respect to individual and group privacy, for public study and use. Combined with recent discoveries of inversion and transposition within the human species, this opens up the potential for using large-scale rearrangements to reconstruct the genealogy tree of the human population.

The specification provides a brief summary of discovered inversions and transpositions within the human population and the computational methods being used by the bio-informatics community to tackle the problem of reconstructing phylogeny trees.

Inversions along a chromosome are frequently observed by comparing closely related species: for example, a comparison between a chimpanzee chromosome and a human chromosome, or a mouse chromosome and a human chromosome. These are generally very long inversions that are observed as reversed gene orders.

Moreover, with the most recent builds of the chimpanzee genome, a total of 1,576 putative regions of inverted orientation, covering more than 154 mega-bases, of all sizes between the human and chimpanzee genomes have been observed. However, inversions have been seen across humans: X chromosome and a 3 Mb inversion on the short arm of the Y chromosome. Human inversions occur at a low but detectable frequency. The ones that are large enough to be detected by conventional cytogenetic analysis occur at a frequency of 1-5 per 10,000 individuals. The inversions across humans are of particular interest, since often the recombination in the inverted segments in heterozygotes lead to heritable disorders.

Secondly, inversions also have a potential for explaining the geographic distribution of the human population: a reconstruction of the prehistoric human colonization of the planet. The X-chromosome inversion is seen in populations of European descent at a frequency of about 18%.

Further, large chromosomal segment inversions have been seen in humans. A paracentric inversion polymorphism spanning larger than a 2.5 Mb segment in chromosome band 8p23.1-8p22 and a 900-Kb inversion on chromosome 17q21-31 have been reported. The second inversion is seen at the rate of 20% in Europeans and almost absent in East Asians and rare in Africans.

Large chromosomal rearrangement polymorphisms, such as, for example deletions or duplications, are apparent by a loss or gain of heterozygosity. However, inversions are difficult to detect and may go unnoticed if the inverted segment is small.

The inversions may occur in coding, non-coding, or intra-gene regions of the chromosome. Hence, a model that tracks the gene orders of the chromosome is inadequate for modeling segment inversions. Instead, these inversions are being discovered and reported in terms of the order of the labeled short tandem repeat polymorphisms.

Further, unlike genes, these markers are not signed. Also, the ancestral segment is unknown. In other words, it is unclear which order of the segment came first.

Translocations have also been observed in humans although these have been mostly of single genes and generally associated with a disorder. It is believed that as individual differences are learned, more such variations, transpositions or inversions, will surface. In fact, these (inversions) may be only the tip of the iceberg.

FIG. 1 illustrates a short tandem repeat polymorphism on two human chromosomal segments. The blocked segment shown here is inverted in a significant fraction of the human population.

Loosely speaking there are two conventional computational approaches to studying the evolutionary relationships of genomes, one of studying the individual gene sequences and the other of studying the arrangement of multiple genes on the genome. A very large amount of literature exists for the first approach (including sequences under the character model), which are not described here to avoid digression.

The second approach of the description of chromosomal inversions in Drosophila had appeared way back in early part of last century. An active interest has been taken in the study of genome rearrangements in the last decade resulting in some very interesting observations and debates in the community.

In the context of genome rearrangements, genomes are viewed as permutations where each integer corresponds to a unique gene or marker. For mono-chromosomal genomes, the most common rearrangement is inversion that is often called reversal in the area of bio-informatics. Without loss of generality, a permutation of length n with i≤j, can be written as $\pi_1$, the inversion on $\pi_1$ defined as $r^{ij}(\pi_1)$ and the transposition on $\pi_1$ defined below as $t^{ijk}(\pi_1)$ where the underlined portion is the reversed or transposed segment.

$$\pi_1 = p_1 p_2 \ldots p_{i-2} p_{i-1} \underline{p_i p_{i+1} p_{i+2} \ldots p_j p_{j+1}} p_{j+2} \ldots p_k p_{k+1} \ldots p_n$$

$$r^{ij}(\pi_1) = p_1 p_2 \ldots p_{i-2} p_{i-1} \underline{p_j p_{j-1} p_{j-2} \ldots p_i} p_{j+1} p_{j+2} \ldots p_k p_{k+1} \ldots p_n$$

$$t^{ijk}(\pi_1) = p_1 p_2 \ldots p_{i-2} p_{i-1} \underline{p_{j+1} p_{j+2} \ldots p_k p_i p_{i+1} p_{i+2} \ldots p_j} p_{k+1} \ldots p_n$$

Clearly, $r^{ij}(r^{ij}(\pi)) = \pi$ leading to the idea of a shortest inversion path between two permutations. This shortest inversion path between $\pi_1$ and $\pi_2$ is the distance between the two given as $D^r(\pi_1, \pi_2)$. However, computing $D^r(\pi_1, \pi_2)$ for a given pair of permutations $\pi_1$ and $\pi_2$ is NP-complete. It has been shown that by supplementing the genes with signs, this problem could be solved in polynomial time by using graph structures termed "hurdles" and "fortresses."

In sequences, the problems of multiple sequence alignment and the construction of the implicit phylogeny tree, have been conventionally separated for simplicity. Such a distinction under the genome rearrangement model is not so obvious. However, breakpoint phylogeny was introduced to study this problem under a simplified cost function of minimizing the number of breakpoints.

Heuristic approaches also have conventionally been applied to this problem. A rich body of literature on inferring phylogenies under the sequence or character models exists, including attempts at using sequence and distance based methods to genome rearrangement problems In this context, a key observation is that the "distance" between two members, or member and ancestor, within the species is small.

SUMMARY OF THE INVENTION

In view of the foregoing and other exemplary problems, drawbacks, and disadvantages of the conventional methods and structures, an exemplary feature of the present invention is to provide methods and systems in which genomic common ancestors are reconstructed.

In a first exemplary aspect of the present invention, a method of reconstructing genomic common ancestors includes constructing a PQ tree structure based upon permutations between two genomes and reconstructing an ancestor genome based upon the PQ tree. The PQ tree includes a first internal node (P node), that allows permutation of the children thereof, and a second internal node (Q node), that maintains unidirectional order of the children thereof.

In a second exemplary embodiment of the present invention, a system for reconstructing genomic common ancestors includes a determination unit that determines a PQ tree structure based upon permutations between two genomes, and a reconstructing unit that reconstructs an ancestor genome based upon the PQ tree structure.

In a third exemplary embodiment of the present invention, a program embodied in a computer readable medium executable by a digital processing unit includes instructions for determining a PQ tree structure based upon permutations between two genomes, and instructions for reconstructing an ancestor genome based upon the PQ tree structure.

An exemplary embodiment of the present invention exploits the peculiarities in the small distances between genomes within a specie to reconstruct a genealogy tree.

An exemplary embodiment of the present invention constructs a minimal consensus PQ tree based upon permutations, which may then be used to represent a genomic ancestry tree.

These and many other advantages may be achieved with the present invention.

BRIEF DESCRIPTION OF THE DRAWINGS

The foregoing and other exemplary purposes, aspects and advantages will be better understood from the following detailed description of exemplary embodiments of the invention with reference to the drawings, in which:

FIGS. 3(a) and 3(b) illustrates permutations 302 and 304 at distance 1 from each other;

FIG. 4(a) illustrates an input order of segments 400;

FIG. 4(b) illustrates that the two segments 2 and 4 on the input of FIG. 4(a) are disjoint;

FIG. 4(c) illustrates that the two segments marked 2-3 and 3-4 on the input of FIG. 4(a) are straddle;

FIG. 4(d) illustrates that the two segments marked 3 and 2-4 on the input of FIG. 4(a) are nested;

FIG. 7 illustrates an algorithm used by an exemplary embodiment of the present invention;

FIG. 9 illustrates an exemplary PQ tree and eight permutations on ten markers;

FIG. 10 illustrates a trace of the algorithm of FIG. 7 upon the PQ trees of FIGS. 8(a) through 8(l);

FIG. 12 illustrates a program embodied in a computer readable medium executable by a digital processing unit in accordance with an exemplary method according to the present invention; and FIG. 13 illustrates a flowchart 1300 in accordance with an exemplary embodiment of the present invention.

DETAILED DESCRIPTION OF EXEMPLARY EMBODIMENTS OF THE INVENTION

Figure 1:
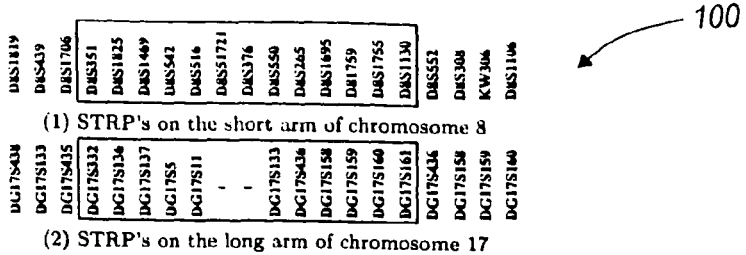
FIG. 1 illustrates short tandem repeat polymorphisms 100 on two human chromosomal segments.
Figure 2:
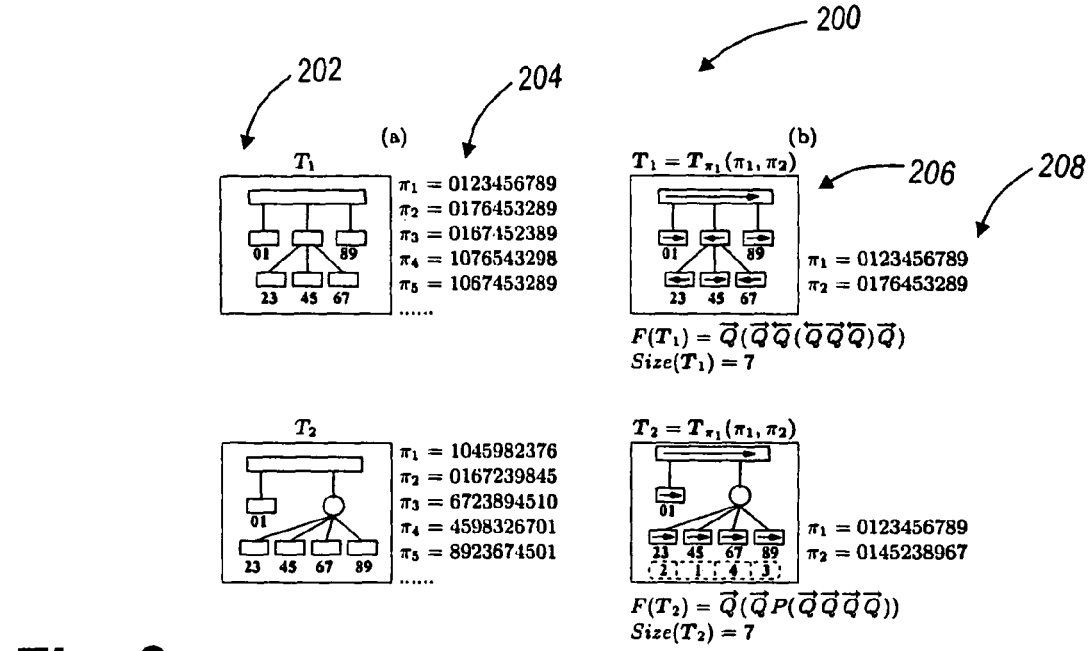
FIGS. 2(a) and 2(b) show examples of oriented PQ trees 200 and how they succinctly describe a pair of permutations.

Referring now to the drawings, and more particularly to FIGS. 1-13, there are shown exemplary embodiments of the methods and systems of the present invention.

The inventors invented a very powerful, yet simple, computational model of the multiple genome rearrangement problem. Since the motivation is from ordered chromosomal segments, the inventors applied this problem to unsigned permutations.

Further, since the inversions and transpositions are within the same species, the distance between the members is observed to be very small. A coalescent approach, which focuses mainly on mutations at a fixed site, is based on the realization that genealogy is usually easier to model backward in time. An exemplary embodiment of the present invention takes a similar approach to a large scale genome rearrangements model.

An exemplary embodiment of this invention is based on a minimal consensus PQ tree of permutations and the observation that the number and size of each permutation (excluding leaf nodes) is O(1) for a small distance between permutations.

An exemplary embodiment of the present invention also provides an annotation scheme (called an "oriented PQ tree"), that helps to uniquely reconstruct the permutations from the tree. Based on this, an exemplary embodiment of the invention poses a problem as a permutation tree construction task and provides a simple branch-and-bound solution.

An exemplary embodiment of the invention provides a genealogy tree and also reconstructs all the common ancestors.

The present specification now provides a brief summary of PQ trees, which may be used as a tool to solve a general consecutive arrangement problem in accordance with an exemplary embodiment of the present invention.

A general consecutive arrangement problem is the following:

Given a finite set X and a collection I of subsets of X, does there exist a permutation $\pi$ of X in which the members of each subset I $\in$ I appear as a consecutive substring of $\pi$?

An efficient linear time algorithm solves this problem using a PQ tree.

A PQ tree is a rooted tree whose internal nodes are of two types: P and Q. The children of a P-node occur in no particular order while those of a Q-node appear in a left to right or right to left order. The figures accompanying this specification designate a P-node by a circle and a Q-node by a rectangle. The leaves of T are labeled bi-jectively by the elements of X.

Two PQ trees T and T' are equivalent, denoted T≡T', if one can be obtained from the other by applying a sequence of the following transformation rules: (1) arbitrarily permute the children of a P-node, and (2) reverse the children of a Q-node.

A frontier F(T), of tree T is the sequence of leaf nodes in a left to right order. For example, in FIG. 2, $F(T_1)=F(T_2)=0123456789$.

C(T), which is the collection of all possible frontiers of equivalent PQ trees, is defined as follows:

$$C(T)=\{F(T')|T'\equiv T\} \quad (1)$$

Let an input be a sequence s of length n defined on a finite alphabet $\Sigma$. A permutation pattern p on s is defined as a set of characters $\sigma_i \epsilon \Sigma$, that appear possibly in different orders at different locations in the input.

For example, let $s=\sigma_1\sigma_4\sigma_2\sigma_3 \ldots \sigma_1\sigma_2\sigma_3\sigma_4$, then $P=\{\sigma_1, \sigma_2, \sigma_3, \sigma_4\}$ is a permutation pattern that appears at the beginning and end of s. $\Pi$ denotes a collection of permutations $\pi_i$. A maximal notation of permutation patterns has been used, which was later shown to have the same structure as PQ trees.

Given $\Pi$, a consensus PQ tree T of $\Pi$, written as $T(\Pi)$, is such that $\Pi \subset C(T)$ and a consensus PQ tree is minimal when there exists no $T' \not\equiv T$ such that $\Pi \subset C(T')$ and $|C(T')|<|C(T)|$.

Of all the equivalent PQ trees in $\overline{T(\Pi)}$, some specific forms are interesting, which are defined below.

A permutation or $\pi$ is "nailed" if the left to right order of $\pi$ is fixed, i.e., the left uniquely refers to one end and right uniquely refers to the other end. Given $\Pi$, $T(\Pi)$ is nailed with respect to $\pi \epsilon \Pi$ if the leaves ordered from left to right is the permutation $\pi$. Clearly, $$T_{\pi_1}(\Pi)=T_{\pi_2}(\Pi), \quad (2)$$

for all $$\pi_1,\pi_2 \epsilon \Pi. \quad (3)$$

An exemplary embodiment of the present invention uses the following convention to reconstruct the two individual permutations from their nailed minimal consensus PQ tree.

Consider two nailed permutations $\pi_1$ and $\pi_2$ and nailed PQ tree $$\vec{T}_{\pi_1}(\Pi=\{\pi_1,\pi_2\}), \quad (4)$$

Without loss of generality, $\vec{T}_{\pi_1}$ is oriented if each Q node is annotated with ($\rightarrow$) or ($\leftarrow$) labels. The ($\rightarrow$) label indicates that the two segments are identical in the nailed permutations $\pi_1$ and $\pi_2$. Similarly, the ($\leftarrow$) label indicates that the two segments are flipped in the nailed permutations $\pi_1$ and $\pi_2$.

Further, a P node with k children is numbered by integers 1 to k denoting the order in which they appear in $\pi_2$ (they appear in the left to right order in $\pi_1$ as depicted in the oriented PQ tree).

FIGS. 2(a) and 2(b) shows examples of oriented PQ trees and how they succinctly describe a pair of permutations. FIG. 2(a) illustrates a PQ tree 202 and a subset of the collection of permutations 204 represented by the tree; and FIG. 2(b) illustrates a nailed and oriented PQ tree 206 and the only two permutations 208 it represents.

A frontier, $F(\vec{T})$, of a nailed and oriented tree $\vec{T}$ is simply the in-order notation of the PQ tree excluding the labeled leafnodes, with the orientation of the Q nodes denoted by a left or right arrow.

Further, two nailed and oriented trees $\vec{T}$ and $\vec{T}'$ are equivalent, denoted as $\vec{T} \equiv \vec{T}'$, if and only if $F(\vec{T})=F(\vec{T}')$. Notice that the leaf nodes (which are labeled 0-9 in FIG. 2(a)) are ignored while checking the equivalency of oriented PQ trees.

The size of $\vec{T}$, denoted as, Size($\vec{T}$) is the number of all the internal nodes (including the root). See FIGS. 2(a) and 2(b) for examples of frontier and size of some $\vec{T}$'s.

Next, the present specification describes the time to construct these PQ trees. Given two permutations $\pi_1,\pi_2$ of length n each, $\vec{T}_{\pi_1}(\{\pi_1,\pi_2\})$ can be constructed in O(n) time.

FIGS. 3(a) and 3(b) illustrates permutations 302 and 304 at distance 1 from each other. Treating the segments as symbols, FIG. 3(a) gives $\pi_1=1234$ and $\pi_2=1324$, with $\vec{T}(\pi_1, \pi_2)$ as shown and FIG. 3(b) gives $\pi_1=123$ and $\pi_2=1(-2)3$, with $\vec{T}(\pi_1,\pi_2)$ as shown. The signed segment does not mean that the individual markers are signed. The algorithm to compute $\vec{T}_{\pi_1}(\{\pi_1,\pi_2\})$ detects the inverted order of the unsigned markers and annotates the segments accordingly.

FIG. 4(a) illustrates an input order of segments (the parent that will be computed from two separate inverted segments in each case that follow). The only three possible configurations of two inversion operations are shown in FIGS. 4(b) to 4(d).

FIG. 4(b) illustrates that the two segments marked 2 and 4 on the input are disjoint. Labeling the two resulting permutations as D1 and D2, the first is $\vec{T}_{D1}(D1, D2)$ and the second is $\vec{T}_{D2}(D1, D2)$.

FIG. 4(c) illustrates that the two segments, marked 2-3 and 3-4 on the input, straddle. Labeling the two resulting permutations as S1 and S2, the first is $\vec{T}_{S1}(S1, S2)$ and the second is $\vec{T}_{S2}(S1, S2)$.

FIG. 4(d) illustrates that the two segments, marked 3 and 2-4 on the input are nested. Labeling the two resulting permutations as C1 and C2, the first is $\vec{T}_{C1}(C1, C2)$ and the second is $\vec{T}_{C2}(C1, C2)$.

Recall that $D'(\pi_1,\pi_2)$ denotes the inversion distance between $\pi_1$ and $\pi_2$. Let $D^t(\pi_1, \pi_2)$ denote the shortest transposition path between the two and let $D(\pi_1,\pi_2)$ denote the shortest number of operations, inversion or transposition, that takes $\pi_1$ to $\pi_2$.

The following theorem is central to an exemplary embodiment of the present invention:

Let $\pi_1$ and $\pi_2$ of size n each, be such that $D(\pi_1,\pi_2)=c$, for some constant c, then there exists only O(1) non-equivalent trees $\vec{T}(\pi_1,\pi_2)$, each of size O(1).

Outline of the Proof:

Let k be the maximum number of distinguishable segments that the input permutations can be split into by the rearrangement operation. FIGS. 3(a) and 3(b) show the c=1 case: for transposition operation, k=4 and for inversion operation, k=3. It is easy to see that k is independent of n and only dependent on c, thus k=O(1). The number of distinct configurations depends only on k. Hence there can only be O(1) distinct configurations.

For each distinct case, consider $\vec{T}(\pi_1,\pi_2)$. The leaves of $\vec{T}$ are partitioned into k sets, and, thus, the number of internal nodes is $\leq$k. Thus, Size($\vec{T}$)=O(k)=O(1).

The detailed description now describes how an exemplary embodiment of the present invention reconstructs ancestor permutations.

(parent $P_c(\Pi)$) ($\pi' \not\in \Pi$)$\epsilon P_c(\Pi)$, is a permutation such that for each $\pi \epsilon \Pi$, $D(\pi,\pi') \leq c$ for some integer $c \geq 0$. Consider the task of computing $P_c(\Pi)$ where $\Pi=\{\pi_1,\pi_2\}$. If $D(\pi_1,\pi_2)=c$, then for each $\pi_p^i \epsilon P_c(\Pi)^i$ is such that $D(\pi_1,\pi_p^i)=c_i$ and $D(\pi_2,\pi_p^i)=c-c_i$, for some $0 \leq c_i \leq c$.

The detailed description now illustrates the use of a tree $\vec{T}(\pi_1,\pi_2)$ to compute a common parent through a simple example in accordance with an exemplary embodiment of the present invention. For simplicity assume c=1 and the only operation permitted is inversion. In FIGS. 4(a)-4(d), only show the possible three cases. The $\vec{T}$ shown are also called masks since they can be mechanically compared to the consensus nailed, oriented PQ trees of the given permutations.

For clarity of exposition, each mask is shown in the two possible forms, when the resulting oriented PQ tree is nailed with respect to $\pi_1$ and then with respect to $\pi_2$. The algorithm to match the oriented PQ tree with a mask is outlined in FIG. 8.

In the algorithm, the data structure for $\vec{T}$ is as follows: (1) $\vec{T}$.type is $\vec{Q}$, $\overleftarrow{Q}$ or P, (2) $\vec{T}$.noc is the number of children of the node, (3) $\vec{T}$.chld[i] is the pointer to the ith child of the node, and (4) $\vec{T}$.Lvs is the leaves of the node, if the children of the node are leaves (else this is empty).

An exemplary embodiment of the present invention works by comparing the candidate tree with the mask, by doing a simultaneous breadth first search of the two trees. The embodiment collects all possible matches with a single mask by using the notation of matching curly braces ("","""): only one of the elements within the curly braces separated by commas is to be considered. For example, the result ans="−4+2+1,+1+3" is to be interpreted as two possible matches −4+2+1 or −4+1+3. If the candidate tree $\vec{T}_c$ was such that its sets of leaf nodes were (abc), (def), (ghi), then the first match gives the parent as ihgdefabc and the second match gives the parent as ihgabcdef.

The working of an exemplary embodiment is best explained through an example. Consider FIGS. 8(a)-8(c): The nailed, oriented PQ tree in FIGS. 8(a) and 8(b) do not match any masks. However, FIG. 8(c) matches mask D1 (or D2) of FIG. 4(b). By matching the first three segments, marked +1, +2 and +3, (0, 23451, 6) are placed in the same order and the fourth segment, marked −4 (789) is reversed giving the parent 0234516987. Thus, the mask can be used to reconstruct a common parent.

Figures 5, 6:
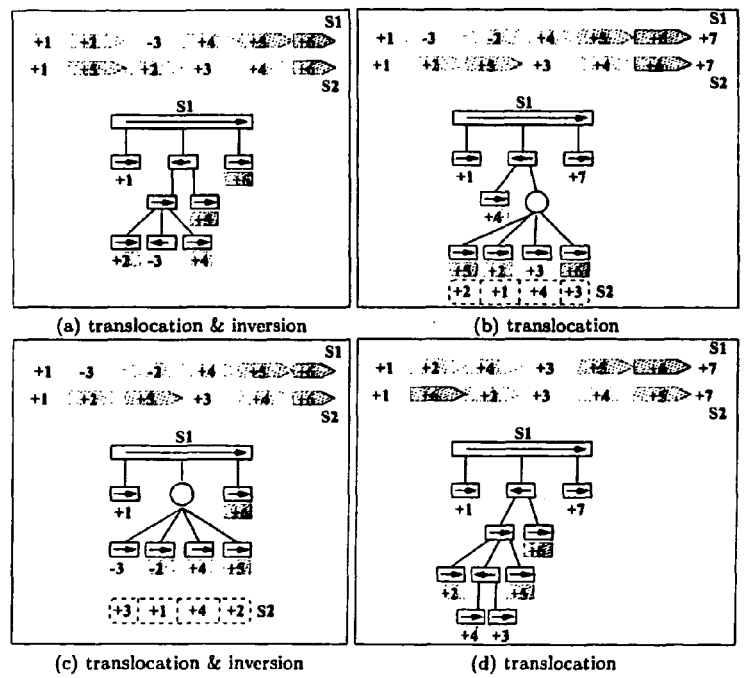
FIG. 5 illustrates the use of masks on some simple examples that involve both inversions and transpositions.
FIG. 6 illustrates an exemplary algorithm to compute a tree (example in FIG. 7)

FIG. 5 illustrates the use of masks on some simple examples that involve both inversions and transpositions. Reconstruction of a common parent: A pair of permutations $\pi_1$ and $\pi_2$ and their common immediate parent $\pi_p$ is shown here.

An inversion is shown by a box and a transposition is shown as segment with a top bar being transposed to a destination shown by a boxed arrow. Although the operation is being shown here on each $\pi_1$ and $\pi_2$ for convenience, the same can be viewed as operations on the parent $\pi_p$ that generates $\pi_1$ and $\pi_2$. A pointer to the PQ trees (masks) that are used to reconstruct the common parent is given in the last column.

The detailed description now presents a very simple branch and bound algorithm to solve a permutation tree construction task using PQ trees.

Input: $\Pi$, a set of m permutations of size n each.
Output: A minimum length tree T(V, E) and a mapping P:(v∈V)→$\Pi$*, sending (v∈V)→($\pi$∈$\Pi$*), where $\Pi \subset \Pi$*.

In the description of the algorithm in FIG. 7, let A denote an array of encoding of trees, indexed by permutation $\pi$. Thus, A[$\pi$'] stores the subtree rooted at v with $\pi$(v)=$\pi$' encoded in the postfix notation as s($\pi$'). Also, assume that the + operator works as follows: +($\Pi$)=$\pi$' where $\Pi$={$\pi_1,\pi_2, \ldots \pi_k$} and s($\pi$')=A($\pi_1$)A($\pi_2$)...A($\pi_k$)k$\pi$', the subtree rooted at $\pi$' in the postfix notation. Lpi($\pi$) is the collection of nodes labeled by $\pi$'∈$\Pi$ reachable from node labeled with $\pi$. Chld($\pi$) is the collection of immediate children of $\pi$. For the sake of clarity of exposition, the outline of the algorithm illustrated in FIG. 7, excludes some implementation details.

The algorithm works by computing common parents of the permutations. It continues the process until no more common parents can be computed. Since the common parents are not unique and there may be multiple trees, the algorithm keeps track of all possible trees in A[ ]. Thus, at the end of the loop for each $\pi$ with Lpi($\pi$)=$\Pi$, s($\pi$) denotes a plausible evolutionary tree.

Figure 8:
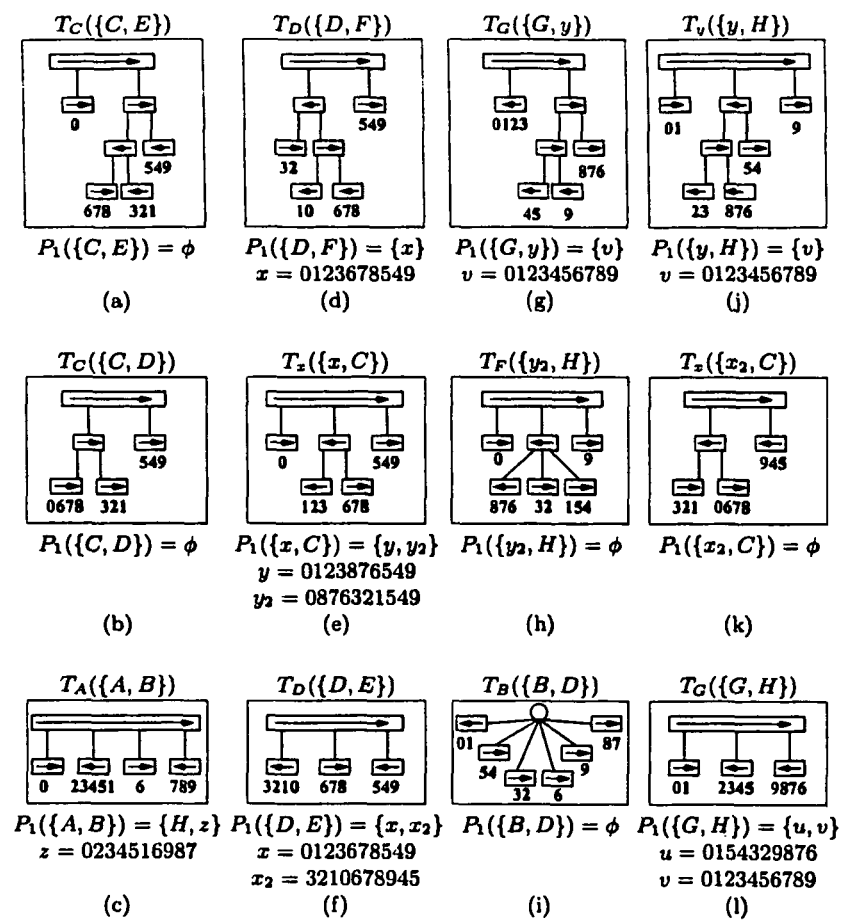
FIGS. 8(a) through 8(l) illustrate finding common parents using PQ trees in accordance with an exemplary embodiment of the present invention.

An example with 8 permutations on 10 markers 900 along with the permutation tree T 902 is illustrated in FIG. 9. For this example, the task of finding common parents using PQ trees is illustrated in FIG. 8 in a few cases. The overall trace of the algorithm is shown in FIG. 10.

Some computations (randomly chosen 12 parent computations) on the input permutations of the example are illustrated by FIG. 9. Permutations A-G are given and permutations u, v, x, $x_2$, y, $y_2$, z are computed in the intermediate steps. Consider (a): The boxed PQ tree is the minimal consensus PQ tree of $\Pi$={C, E} nailed with respect to C and the parent at distance 1 is given as $P_1(\Pi)$. (b)-(1) are to be similarly interpreted.

In consideration of mutations, it may be assumed that the permutation on the markers will also include the specific allelic form it represents, i.e., say the copy number in case of micro satellites and the nucleic acid base in case of SNP's (Single Nucleotide Polymorphism). Let $D^a(\pi_1,\pi_2)$ denote the number of markers that differ in their allelic form. For example, if $\pi_1=1^a 2^a 3^b 4^c 5^a$, $\pi_2=1^a 3^a 2^a 5^c 4^c$, where the superscript denotes an encoding of the allelic form, then $D^a(\pi_1,\pi_2)$ =2 since markers 3 and 5 vary in their allelic forms.

An exemplary embodiment of the present invention may be extended to include mutations. In fact, in practice, the problem may be simplified by the use of mutations since, this will help time-order the events.

An exemplary method of the present invention reconstructs the genealogy tree without using mutations and then resolves the tree using the mutation information.

An exemplary embodiment of the present invention provides a systematic way of studying large-scale genome rearrangements to construct a genealogy tree (say, within a species). The problem is motivated by the discoveries of large number of inversions and transpositions within the human population.

Figure 11:
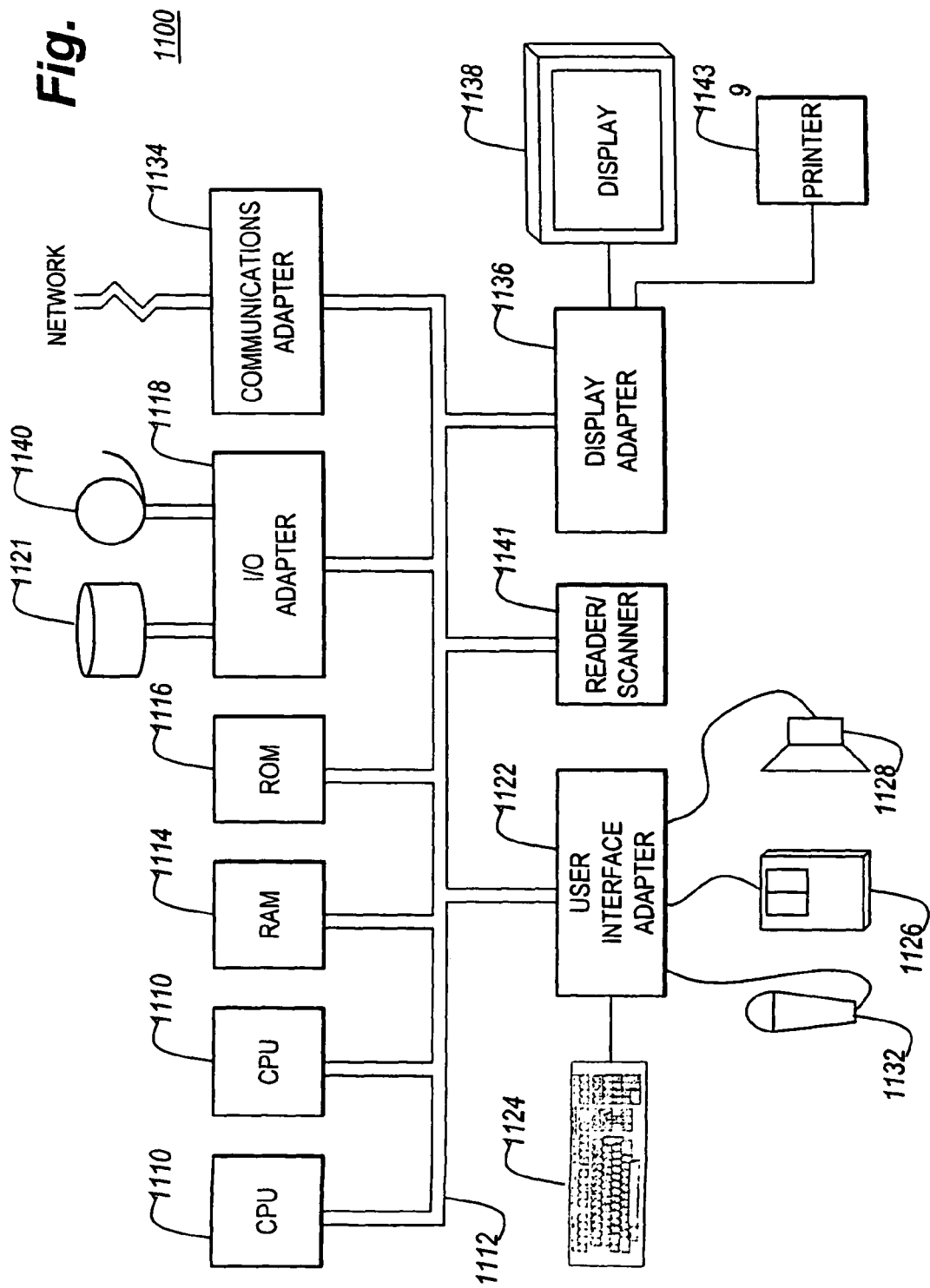
FIG. 11 illustrates an exemplary hardware/information handling system 1100 for incorporating the present invention therein.

Referring now to FIG. 11, system 1100 illustrates a typical hardware configuration which may be used for implementing the inventive system and method for reconstructing genomic common ancestors. The configuration has preferably at least one processor or central processing unit (CPU) 1110. The CPUs 1102 are interconnected via a system bus 1112 to a random access memory (RAM) 1114, read-only memory (ROM) 1116, input/output (I/O) adapter 1118 (for connecting peripheral devices such as disk units 1121 and tape drives 1140 to the bus 1112), user interface adapter 1122 (for connecting a keyboard 1124, mouse 1126, speaker 1128, microphone 1132, and/or other user interface device to the bus 1112), a communication adapter 1134 for connecting an information handling system to a data processing network, the Internet, and Intranet, a personal area network (PAN), etc., and a display adapter 1136 for connecting the bus 1112 to a display device 1138 and/or printer 1139. Further, an automated reader/scanner 1141 may be included. Such readers/scanners are commercially available from many sources.

In addition to the system described above, a different aspect of the invention includes a computer-implemented method for performing the above method. As an example, this method may be implemented in the particular environment discussed above.

Such a method may be implemented, for example, by operating a computer, as embodied by a digital data processing apparatus, to execute a sequence of machine-readable instructions. These instructions may reside in various types of signal-bearing media.

Thus, this aspect of the present invention is directed to a programmed product, including signal-bearing media tangibly embodying a program of machine-readable instructions executable by a digital data processor to perform the above method.

Such a method may be implemented, for example, by operating the CPU 1110 to execute a sequence of machine-readable instructions. These instructions may reside in various types of signal bearing media.

Thus, this aspect of the present invention is directed to a programmed product, comprising signal-bearing media tangibly embodying a program of machine-readable instructions executable by a digital data processor incorporating the CPU 110 and hardware above, to perform the method of the invention.

This signal-bearing media may include, for example, a RAM contained within the CPU 1110, as represented by the fast-access storage for example. Alternatively, the instructions may be contained in another signal-bearing media, such as a magnetic data storage diskette 1200 or CD-ROM 1202, (FIG. 12), directly or indirectly accessible by the CPU 1110.

Whether contained in the computer server/CPU 1110, or elsewhere, the instructions may be stored on a variety of machine-readable data storage media, such as DASD storage (e.g., a conventional "hard drive" or a RAID array), magnetic tape, electronic read-only memory (e.g., ROM, EPROM, or EEPROM), an optical storage device (e.g., CD-ROM, WORM, DVD, digital optical tape, etc.), paper "punch" cards, or other suitable signal-bearing media including transmission media such as digital and analog and communication links and wireless. In an illustrative embodiment of the invention, the machine-readable instructions may comprise software object code, complied from a language such as "C," etc.

FIG. 13 illustrates a flowchart 1300 of an exemplary method in accordance with the present invention. The flowchart 1300 starts at step 1302 and continues to step 1304. In step 1304, the method determines a PQ tree structure based upon permutations between two genomes and continues to step 1306. In step 1306, the method reconstructs an ancestor genome based upon the PQ tree structure and continues to step 1308, where the method stops.

Exemplary embodiments of the present invention may be used to reconstruct common genomic ancestors. The embodiments may also exploit the peculiarities in the small distances between genomes within a specie to reconstruct a geneology tree.

While the invention has been described in terms of several exemplary embodiments, those skilled in the art will recognize that the invention can be practiced with modification.

Further, it is noted that, Applicant's intent is to encompass equivalents of all claim elements, even if amended later during prosecution.

What is claimed is:

1. A method of reconstructing a genealogy tree, the method comprising:
   determining, using a processor on a computer, a PQ tree structure based upon permutations between two genomes; and
   reconstructing, using a processor on a computer, an ancestor genome based upon the PQ tree structure, wherein said PQ tree structure comprises:
      a first internal node (P node) that allows a permutation of children thereof; and
      a second internal node (Q node) that maintains a unidirectional order of the children thereof, and
   wherein said reconstructing comprises matching said PQ tree structure to a structure represented by one of a set of masks.

2. The method of claim 1, wherein said PQ tree structure comprises a minimal consensus, nailed, and oriented PQ tree.

3. The method of claim 1, wherein said reconstructing further comprises constructing an ancestor genome based upon a matching mask.

4. The method of claim 1, wherein each mask in said set of masks is based upon a predetermined maximum number of permitted transformations.

5. The method of claim 1 stored and executable on a computer readable medium, wherein the children of the P node arbitrarily permute and the children of the Q node occur in a left to right order.

6. The method of claim 1, wherein:
   the set of masks provide a mapping of maximal permutation patterns to the PQ tree structure, further comprising identifying the permutation patterns in a maximal form,
   the method of reconstructing the genealogy tree being stored on a tangible computer readable medium and executed by the processing unit of a computer.

7. The method of claim 1, further comprising storing the method of reconstructing the genealogy tree on a tangible storage medium,
   wherein the reconstructing of the ancestor genome is outputted to a display device from the tangible storage medium by the processor.

8. A system for reconstructing a genealogy tree, said system comprising a processor for executing instruction, said system comprising:
   a determination unit, stored on a tangible computer readable storage medium, that determines a PQ tree structure based upon a permutation between two genomes; and
   a reconstructing unit, stored on the tangible computer readable storage medium, that reconstructs an ancestor genome based upon the PQ tree structure and permutation patterns in maximal form, wherein said PQ tree structure comprises:
      a first internal node, comprising a P node, that allows a permutation of children thereof; and
      a second internal node, comprising a Q node, that maintains a unidirectional order of the children thereof,
   wherein said reconstructing unit matches said PQ tree structure to a structure represented by one of a set of masks.

9. The system of claim 8, wherein said reconstructing unit, stored on the tangible computer readable storage medium, constructs an ancestor genome based upon a matching mask.

10. The system of claim 8, wherein each mask in said set of masks is based upon a predetermined maximum number of permitted transformations.

11. A tangible computer readable storage medium embodying a set of instructions executable by a processing unit, to execute a method of reconstructing a genealogy tree, said method comprising:
   determining, by using the processing unit, a PQ tree structure based upon permutations between two genomes; and reconstructing, by using the processing unit, an ancestor genome based upon the PQ tree structure,
wherein said reconstructing the ancestor genome comprises mapping maximal permutation patterns to the PQ tree structure, and
said PQ tree structure comprises:
a first internal node (P node) that allows a permutation of children thereof; and
a second internal node (Q node) that maintains a unidirectional order of the children thereof,
wherein said reconstructing comprises matching said PQ tree structure to a structure represented by one of a set of masks.

12. The storage medium of claim 11, wherein reconstructing further comprises constructing an ancestor genome based upon a matching mask.

13. The storage medium of claim 11, wherein each mask in said set of masks is based upon a predetermined maximum number of permitted transformations.

14. A system for reconstructing a genealogy tree, said system comprising a processor for executing instruction, said system comprising:
a determination unit, stored on a tangible computer readable storage medium, that determines a PQ tree structure based upon a permutation between two genomes; and
a reconstructing unit, stored on the tangible computer readable storage medium, that reconstructs an ancestor genome based upon the PQ tree structure and permutation patterns in maximal form, wherein said PQ tree structure comprises:
a first internal node, comprising a P node, that allows a permutation of children thereof; and
a second internal node, comprising a Q node, that maintains a unidirectional order of the children thereof,
wherein said reconstructing unit matches said PQ tree structure to a structure represented by a mask.

* * * * *